US012171498B2

(12) United States Patent
Lenich

(10) Patent No.: US 12,171,498 B2
(45) Date of Patent: Dec. 24, 2024

(54) PRESENTATION DEVICE FOR DISPLAYING A GRAPHICAL PRESENTATION OF AN AUGMENTED REALITY

(71) Applicant: Siemens Healthcare GmbH, Erlangen (DE)

(72) Inventor: Tobias Lenich, Nuremberg (DE)

(73) Assignee: Siemens Healthineers AG, Forchheim (DE)

( * ) Notice: Subject to any disclaimer, the term of this patent is extended or adjusted under 35 U.S.C. 154(b) by 387 days.

(21) Appl. No.: 17/841,232

(22) Filed: Jun. 15, 2022

(65) Prior Publication Data

US 2022/0409283 A1    Dec. 29, 2022

(30) Foreign Application Priority Data

Jun. 24, 2021 (DE) ...................... 10 2021 206 568.6

(51) Int. Cl.
*A61B 34/10* (2016.01)
*A61B 90/00* (2016.01)
(Continued)

(52) U.S. Cl.
CPC .............. *A61B 34/10* (2016.02); *A61B 90/36* (2016.02); *A61B 90/39* (2016.02); *A61B 90/50* (2016.02);
(Continued)

(58) Field of Classification Search
CPC ......... A61B 34/10; A61B 90/36; A61B 90/39; A61B 90/50; A61B 2034/105;
(Continued)

(56) References Cited

U.S. PATENT DOCUMENTS

2014/0191929 A1    7/2014 Kim
2021/0096638 A1    4/2021 O'hern et al.
(Continued)

FOREIGN PATENT DOCUMENTS

DE      102021206565 A1    12/2022
WO        2021061441 A1     4/2021

OTHER PUBLICATIONS

Sielhorst et al., "Advanced Medical Displays: A Literature Review of Augmented Reality", Journal of Display Technology, vol. 4, No. 4, Dec. 2008 (Year: 2008).*

(Continued)

*Primary Examiner* — Qian Yang

(74) *Attorney, Agent, or Firm* — Lempia Summerfield Katz LLC

(57) ABSTRACT

A presentation device for displaying a graphical presentation of an augmented reality is disclosed. The presentation device includes a recording unit, a first display unit, and a processing unit. The recording unit is configured to capture a relative positioning of the first display unit in respect of a presentation area and capture a second set of graphical information. The processing unit is configured to generate an augmented reality based on a received dataset, supply a graphical presentation of the augmented reality by virtual mapping to the presentation area, and adjust the augmented reality and/or the graphical presentation thereof as a function (Continued)

of the second set of graphical information. The first display unit is at least partially transparent and is configured to display the graphical presentation of the augmented reality.

17 Claims, 4 Drawing Sheets

(51) Int. Cl.
*A61B 90/50* (2016.01)
*G06T 19/00* (2011.01)
*G06T 19/20* (2011.01)
(52) U.S. Cl.
CPC ............ *G06T 19/006* (2013.01); *G06T 19/20* (2013.01); *A61B 2034/105* (2016.02); *A61B 2090/365* (2016.02); *A61B 2090/502* (2016.02); *G06T 2219/2016* (2013.01)
(58) Field of Classification Search
CPC ........ A61B 2090/365; A61B 2090/502; A61B 90/361; A61B 90/96; A61B 2090/372; G06T 19/006; G06T 19/20; G06T 2219/2016; G06T 2210/41
See application file for complete search history.

(56) References Cited

U.S. PATENT DOCUMENTS

| 2021/0137350 | A1* | 5/2021 | Inglis | A61B 1/00016 |
| 2021/0330388 | A1* | 10/2021 | Den Hartog | G06V 20/20 |
| 2021/0330395 | A1* | 10/2021 | Govari | A61B 1/00009 |
| 2021/0358220 | A1* | 11/2021 | Berger | G06T 7/30 |
| 2022/0414994 | A1 | 12/2022 | Regensburger | |

OTHER PUBLICATIONS

Andersen et al., "Medical telementoring using an augmented reality transparent display", Surgery, vol. 159, No. 6 (Year: 2016).*

Ma et al., "Moving-Tolerant Augmented Reality Surgical Navigation System Using Autostereoscopic Three-Dimensional Image Overlay", IEEE Journal of Biomedical and Health Informatics, vol. 23, No. 6, Nov. 2019 (Year: 2019).*

* cited by examiner

PRESENTATION DEVICE FOR DISPLAYING A GRAPHICAL PRESENTATION OF AN AUGMENTED REALITY

The present patent document claims the benefit of German Patent Application No. 10 2021 206 568.6, filed Jun. 24, 2021, which is hereby incorporated by reference in its entirety.

TECHNICAL FIELD

The present disclosure relates to a presentation device for displaying a graphical presentation of an augmented reality, a system, and a method for supplying a graphical presentation of an augmented reality.

BACKGROUND

For the realistic presentation of medical information, (e.g., of medical image data of an object under examination), increasing use is being made of presentations of an augmented reality (AR). Here, real objects, (e.g., medical objects and/or an object under examination), are frequently overlaid with virtual data, in particular medical image data and/or virtual objects and are presented in a display. For a realistic presentation with a high level of immersion, a precise registration between the virtual data and the real objects is necessary.

A graphical presentation of preoperative and/or intraoperative image data of an object under examination in the augmented reality may be used to assist medical personnel, (e.g., a physician), in interventional and/or surgical procedures. However, the disadvantage of this is frequently that the image data to be displayed by the device for the presentation of the augmented reality, in particular in real time, has to be received and processed by a supply unit and/or a medical imaging device. This may be disadvantageously limited by an available transmission bandwidth, in particular when the image data is supplied, (e.g., simultaneously), to multiple devices for the presentation of an augmented reality. Further, an image quality of the image data to be displayed by the device for the presentation of the augmented reality may as a result also be disadvantageously reduced. A delay between recording the image data, in particular the intraoperative image data, of the object under examination and displaying it in the augmented reality and/or the reduced image quality may lead to a miscoordination during the interventional and/or surgical procedure. As a result, the risk of injury to the object under examination may be increased.

In a medical environment, it may be necessary for three-dimensionally (3D) resolved image data of the object under examination to be viewed simultaneously by multiple viewers among the medical personnel. For this, use may be made of a 3D monitor in combination with stereoscopic filter glasses, which may be worn by the medical personnel. The 3D monitor may supply two individual stereoscopic images, which, by the filter glasses, may be stereoscopically captured for the multiple viewers among the medical personnel. However, the disadvantage of this is the failure to adjust the individual stereoscopic images to the, in particular current, viewing points of the multiple viewers. As a result, an unrealistic and/or insufficient depth perception may arise, in particular as a function of the viewing points, when viewing the three-dimensionally resolved image data on the 3D monitor.

In a medical environment, in particular a surgical and/or interventional environment, (e.g., an operating room), there may moreover be multiple monitors displaying different data, in particular image data, of the object under examination. In this case, it may not be possible to identify the data displayed by the monitors without a communicative coupling to a supply unit for the supply of the data to the monitors.

SUMMARY AND DESCRIPTION

The object of the disclosure is hence to enable a content-based adjustment of an augmented reality.

The scope of the present disclosure is defined solely by the appended claims and is not affected to any degree by the statements within this summary. The present embodiments may obviate one or more of the drawbacks or limitations in the related art.

A first aspect of the disclosure relates to a presentation device for displaying a graphical presentation of an augmented reality. In this case, the presentation device has a recording unit, a first display unit, and a processing unit. In an operating state of the presentation device, a second display unit shows, in a presentation area, a first set of graphical information as visible and a second set of graphical information as a function of the first set of graphical information and as hidden. Further, the recording unit is configured to capture a relative positioning of the first display unit in respect of the presentation area of the second display unit and the second set of graphical information. Furthermore, the processing unit is configured to receive a dataset. Moreover, the processing unit is configured to generate the augmented reality based on the dataset. Further, the processing unit is configured to supply a graphical presentation of the augmented reality by virtual mapping of the augmented reality to the presentation area of the second display unit on the basis of the relative positioning. Moreover, the processing unit is configured to adjust the augmented reality and/or the graphical presentation of the augmented reality as a function of the second set of graphical information. The first display unit is configured to be at least partially transparent. Further, the first display unit is configured to display the graphical presentation of the augmented reality in an at least partial overlay with the presentation area of the second display unit.

The second display unit may have a screen and/or monitor and/or projector and/or projection area. In this case, the presentation area of the second display unit may include the projection area and/or a display panel of the screen and/or of the monitor. In particular, the presentation area of the second display unit may include a limited area in which the first and the second sets of graphical information may be displayed. In this case, the presentation area of the second display unit may, at least in part, be flat, in particular completely flat, in particular level, or curved. The first set of graphical information may include image data, in particular medical image data, and/or text information, for example, operating parameters and/or object parameters of an object, in particular a medical object, and/or metadata on the medical image data.

The second display unit may display the first and the second sets of graphical information in the operating state of the presentation device substantially simultaneously, in particular interleaved in time and/or space, or sequentially. Further, the display of the second set of graphical information may advantageously take place in a wavelength range outside a light spectrum detectable by the human user, for example, in an infrared range. The temporal interleaving may describe a display, in particular a repeated display, of the second set of graphical information within a temporal sequence of the display of the first set of graphical information. In this case, the second display unit may be configured to display the second set of graphical information infrequently and/or for a brief time within the sequence of the display of the first set of graphical information, such that the second set of graphical information is not detectible for the human user. The spatially interleaved display of the second set of graphical information with the first set of graphical information may take place, for example, row by row and/or column by column. In this case, the second display unit may advantageously be configured to predefine a spatial resolution of the second set of graphical information, such that the second set of graphical information in the spatially interleaved display is not detectible for the human user. The second display unit may advantageously be configured to display the second set of graphical information without any influence, detectible for the human user, on the first set of graphical information. Further, the second display unit may display the first set of graphical information in the operating state of the presentation device as visible, in particular so that it is detectible for the human user, in the presentation area.

The second display unit may advantageously be configured to display the second set of graphical information as a function of the first set of graphical information, for example, as a function of a content and/or an origin and/or a presentation and/or a positioning of the first set of graphical information.

The recording unit may advantageously be configured to capture a spatial positioning of the first and the second display unit, in particular the presentation area of the second display unit. The spatial positioning of the first and the second display unit may in each case describe a spatial position and/or orientation of the first and the second display unit in a coordinate system of the recording unit. Further, the recording unit may be configured to determine the relative positioning of the first display unit in respect of the presentation area of the second display unit on the basis of the captured spatial positionings of the first and the second display unit.

Alternatively, the recording unit may be configured to capture the spatial positioning of the second display unit, in particular the presentation area of the second display unit, in respect of the first display unit. In this case, the recording unit may be arranged in a defined manner in respect of the first display unit, in particular attached to the first display unit and/or integrated at least partially into the first display unit. As a result, the recording unit may be configured to directly capture the relative positioning of the first display unit in respect of the presentation area of the second display unit.

The relative positioning of the first display unit in respect of the presentation area of the second display unit may describe a spatial position and orientation, in particular a three-dimensional spatial position and orientation, of the presentation area in a coordinate system of the first display unit. The relative positioning of the first display unit in respect of the presentation area of the second display unit may advantageously include information on a spatial distance between the first display unit, in particular an origin of the coordinate system of the first display unit, and the presentation area of the second display unit, in particular a reference point, for example, a center point or corner point, of the presentation area. Further, the relative positioning may include information on an angle, in particular a viewing angle, of the first display unit in respect of the presentation area of the second display unit, in particular a normal vector in the reference point of the presentation area.

The recording unit may further be configured to capture the second set of graphical information, in particular simultaneously with the relative positioning. The capture of the second set of graphical information may include a capture of a spatial positioning, in particular a current spatial positioning, of the second set of graphical information in respect of the presentation area of the second display unit. Alternatively, or additionally, the capture of the second set of graphical information may include a readout of the second set of graphical information, in particular of a graphical data storage medium.

The processing unit may advantageously be communicatively coupled to the first display unit and the recording unit. The receipt of the dataset may include a capture and/or readout of a computer-readable data store and/or a receipt from a data storage unit, for example, a database. Further, the dataset may be supplied by a medical imaging device. For this, the processing unit may have an interface.

The dataset may include one or more of medical data, image data, image parameters, (e.g., metadata), model data, (e.g., a patient model and/or organ model and/or tissue model), model parameters, text data, (e.g., operating parameters and/or object parameters of an object, in particular a medical object), or patient information, (e.g., anamnesis data and/or diagnostic data and/or physiological information).

The processing unit may advantageously be configured to generate the augmented reality having at least one virtual object, in particular multiple virtual objects, based on the dataset. In this case, the augmented reality may include a virtual arrangement, in particular a two-dimensional and/or three-dimensional virtual arrangement, of the at least one virtual object, in particular of the multiple virtual objects, in the coordinate system of the first display unit. The processing unit may advantageously be configured to generate the at least one virtual object having geometric and/or anatomical and/or textual and/or graphical features of the dataset. Further, the processing unit may be configured to register the augmented reality, in particular the at least one virtual object, with the presentation area of the second display unit, in particular with the first and/or second sets of graphical information.

The processing unit may further be configured to supply the graphical presentation of the augmented reality by virtual mapping of the augmented reality to the presentation area of the second display unit on the basis of the relative positioning. In this case, the graphical presentation may include a two-dimensional and/or three-dimensional, in particular stereoscopic, presentation of the augmented reality on the first display unit. The virtual mapping of the augmented reality to the presentation area of the second display unit may include a virtual arrangement of the at least one virtual object in the presentation area of the second display unit. Moreover, the virtual mapping for the supply of the graphical presentation of the augmented reality may be based on a virtual projection mapping and/or ray tracing of the at least one virtual object to the presentation area of the second display unit in accordance with the relative positioning.

The supply of the graphical presentation of the augmented reality may include storage on a computer-readable storage medium and/or a transfer to the first display unit.

The processing unit may further be configured to adjust the augmented reality and/or the graphical presentation of the augmented reality as a function of the second set of graphical information. The processing unit may be configured to generate, in particular to determine and/or select, the at least one virtual object, in particular the multiple virtual objects, as a function of the second set of graphical information on the basis of the dataset. Further, the processing unit may be configured to supply the graphical presentation of the augmented reality by virtual mapping of the augmented reality to the presentation area of the second display unit, additionally on the basis of the second set of graphical information. In particular the processing unit may be configured to adjust the virtual mapping of the augmented reality to the presentation area of the second display unit, for example, the virtual projection mapping and/or the ray tracing of the at least one virtual object, additionally on the basis of the second set of graphical information.

The first display unit may advantageously be configured to display the graphical presentation of the augmented reality, in particular two-dimensionally or three-dimensionally. In particular the first display unit may be configured for the stereoscopic display of the graphical presentation of the augmented reality. The first display unit may advantageously be configured to display real, in particular representational, objects, in particular the presentation area of the second display unit, with the graphical presentation of the augmented reality at least partially overlaid and in a display. For this, the first display unit may have a screen and/or a projector and/or a projection area. The first display unit may advantageously be configured as glasses, in particular data glasses, and/or a helmet, in particular a data helmet, and/or a screen. Further, the first display unit may be configured to be portable, in particular to be carried by a user. In this case, the first display unit may be configured to be at least partially transparent, in particular translucent and/or see-through. Further, the first display unit may be configured to be arranged in a field of view of the user.

The proposed form of embodiment may advantageously enable an adjustment, in particular a content-based adjustment, of the augmented reality and/or of the graphical presentation of the augmented reality to the first set of graphical information. In this case, the second set of graphical information, which is displayed as hidden in the presentation area, in particular without visible influence on the first set of graphical information, may be configured for the transmission, in particular the optical transmission, of information to the recording unit as a function of the first set of graphical information.

In a further advantageous form of embodiment of the proposed presentation device, the recording unit may be arranged at a distance from the first and the second display unit. Alternatively, the recording unit may be integrated at least partially into the first display unit.

In a first variant, the recording unit may be arranged at a distance from the first and the second display unit, in particular stationary in respect of a space in which the first and the second display unit are arranged in an operating state of the presentation device. The recording unit may advantageously be arranged, in particular positioned, such that the first and the second display unit, in the operating state of the presentation device, are arranged in a capture region of the recording unit. As a result, the recording unit may be configured to capture in each case the spatial positioning of the first and the second display unit. When the recording unit is arranged at a distance from the first and the second display unit, the recording unit may advantageously be configured for the capture, in particular the simultaneous capture, of the spatial positioning of multiple, in particular similar or different, presentation devices.

In a second variant, the recording unit may be integrated at least partially into the first display unit. In this case, the recording unit may have a defined, in particular stationary, arrangement in respect of the first display unit. The recording unit may advantageously be integrated at least partially into the first display unit, such that the second display unit, in particular the presentation area of the second display unit, is arranged in the operating state of the presentation device in the capture region of the recording unit. As a result, the recording unit may be configured to directly capture the relative positioning between the first and the second display unit.

In a further advantageous form of embodiment of the proposed presentation device, the recording unit may have an optical sensor for the capture of the second set of graphical information.

The optical sensor may advantageously be configured as a camera, for example, as a 2D camera and/or an omni-directional camera and/or a 3D camera, in particular a stereo camera and/or a depth camera and/or a time-of-flight-camera (TOF camera), which is configured for the capture, in particular the optical capture, at least in part, of the presentation area of the second display unit. The optical sensor may advantageously have a sensitivity, in particular a spectral sensitivity, and/or recording frequency and/or resolution which is configured to capture the second set of graphical information displayed as hidden in the operating state of the presentation device. In particular, the optical sensor may be configured to capture only the second set of graphical information displayed as hidden. Alternatively, the optical sensor may be configured to capture the second set of graphical information displayed as hidden, and visible light, in particular additionally the first set of graphical information.

The optical sensor may advantageously be configured to differentiate, in particular filter, the second set of graphical information from the first set of graphical information. The differentiation, in particular filtering, of the second set of graphical information from the first set of graphical information may take place on the basis of identification features, for example, a graphical and/or optical encoding, and/or thanks to a spectral and/or temporal and/or spatial separation. A spectral separation may be enabled, for example, by displaying the first and second sets of graphical information in different, in particular adjoining or spaced-apart, wavelength ranges and/or having different polarizations in the presentation area of the second display unit. Moreover, the temporal and/or spatial separation may be enabled by a temporally and/or spatially interleaved display of the first and the second sets of graphical information in the presentation area of the second display unit.

The proposed form of embodiment may advantageously enable a robust and precise capture of the second set of graphical information.

In a further advantageous form of embodiment of the proposed presentation device, the recording unit may have a further optical and/or electromagnetic and/or acoustic sensor for the capture of the relative positioning.

For example, the recording unit may have a further optical sensor configured as a camera, in particular a 2D camera and/or an omni-directional camera and/or a 3D camera, in particular a stereo camera and/or a depth camera and/or a time-of-flight camera (TOF camera), which is configured for the capture, in particular the optical capture, at least in part, of the first and/or second display unit. The further optical sensor for the capture of the relative positioning may be the same as or different from the optical sensor for the capture of the second set of graphical information. In particular the further optical sensor for the capture of the relative positioning may be the optical sensor for the capture of the second set of graphical information. Furthermore, the recording unit may have an electromagnetic sensor which may be configured to locate the first and/or the second display unit on the basis of electromagnetic waves, in particular a change and/or interference by electromagnetic waves. Further, the recording unit may have an acoustic, in particular ultrasound-based, sensor which is configured to emit a defined ultrasound field and to capture the relative positioning on the basis of a reflected portion of the ultrasound field.

The proposed form of embodiment may enable a precise capture of the relative positioning of the first display unit in respect of the presentation area of the second display unit.

In a further advantageous form of embodiment of the proposed presentation device, the recording unit may be configured to capture the relative positioning on the basis of representational features of the first and/or the second display unit and/or on the basis of the second set of graphical information.

The representational features of the first and/or the second display unit may include a contour and/or a shape and/or a material property and/or a texture, for example, a reflectivity and/or absorption capacity. Furthermore, the first and/or the second display unit may have a representational, in particular two-dimensional or three-dimensional, marker structure which in a defined arrangement is attached to the first and/or second display unit and/or is at least partially integrated. The recording unit may advantageously be configured for the capture of a spatial positioning, in particular a spatial position and/or orientation and/or pose, of the respective marker structure.

The second set of graphical information may advantageously be at least partially stationary in respect of the presentation area. In this case, the recording unit may be configured to capture the relative positioning of the first display unit in respect of the presentation area of the second display unit on the basis of the captured second set of graphical information.

The proposed form of embodiment may enable a particularly robust and at the same time precise capture of the relative positioning of the first display unit in respect of the presentation area of the second display unit.

In a further advantageous form of embodiment of the proposed presentation device, the second set of graphical information may have a graphical data storage medium. In this case, the graphical data storage medium may contain information on the first set of graphical information.

The graphical data storage medium may advantageously have a graphical, in particular one-dimensional or two-dimensional, encoding. Moreover, the graphical data storage medium may be encoded on the basis of time and/or color and/or may be intensity-encoded. In this case, the graphical data storage medium may be configured, for example, as a barcode and/or quick response code (QR code). The graphical data storage medium may advantageously supply, in particular by the graphical encoding, the information on the first set of graphical information to the recording unit. In this case, the recording unit may advantageously be configured to decode the captured graphical data storage medium. Moreover, the graphical data storage medium may have a graphical positioning mark which is configured to mark a position and/or orientation of the graphical data storage medium. The recording unit may advantageously be configured to capture the positioning of the graphical data storage medium in the presentation area of the second display unit on the basis of the graphical positioning mark. Moreover, the recording unit may be configured to capture the relative positioning of the first display unit in respect of the presentation area of the second display unit on the basis of the graphical positioning mark of the graphical data storage medium.

The information on the first set of graphical information may contain origin information and/or presentation information on the first set of graphical information. In this case, the origin information may contain information on a source of the first set of graphical information, for example, a medical imaging device for recording and/or supplying the first set of graphical information. In particular the parameter may contain metadata on the first set of graphical information. Further, the origin information may contain a recording parameter for the first set of graphical information. Moreover, the origin information may contain positioning information which, for example, describes a spatial position and/or orientation and/or pose and/or a spatial recording range of the source, in particular of the medical imaging device for recording and/or supplying the first set of graphical information. Furthermore, the information may include patient information, for example, anamnesis data and/or diagnostic data and/or physiological information, for an object under examination mapped and/or modeled in the first set of graphical information. The presentation information may further contain information on the display of the first set of graphical information, for example, an image frequency and/or a resolution and/or an encoding of image values, for example, of a color encoding or a grayscale encoding.

The processing unit may advantageously be configured to adjust the augmented reality and/or the graphical presentation of the augmented reality as a function of the information on the first set of graphical information, which may be captured by the graphical data storage medium. The adjustment, in particular the content-based adjustment, of the augmented reality may include a determination of the at least one virtual object as a function of the information on the first set of graphical information. Further, the adjustment, in particular the content-based adjustment, of the graphical presentation of the augmented reality may include an adjustment of the virtual mapping as a function of the information on the first set of graphical information.

The proposed form of embodiment may especially efficiently enable the content-based adjustment of the augmented reality to the first set of graphical information.

In a further advantageous form of embodiment of the proposed presentation device, the graphical presentation of the augmented reality may contain a graphical presentation of at least one virtual object of the augmented reality. Moreover, the processing unit may be configured to determine the at least one virtual object on the basis of the second set of graphical information. Alternatively, or additionally, the processing unit may be configured to adjust a resolution and/or scaling and/or size and/or positioning of the graphical presentation of the at least one virtual object on the basis of the second graphical presentation.

In this case, the determination of the at least one virtual object on the basis of the second set of graphical information may include a filtering, in particular a content-based and/or graphical filtering, and/or a reconstruction of the dataset. Alternatively, or additionally, the processing unit may be configured to adjust the resolution, in particular the spatial and/or temporal resolution, and/or scaling and/or the size and/or positioning of the graphical presentation of the at least one virtual object on the basis of the second set of graphical information. For example, the processing unit may be configured to adjust the spatial and/or temporal resolution and/or size and/or positioning of the graphical presentation of the at least one virtual object as a function of a spatial and/or temporal resolution and/or size and/or positioning of the first set of graphical information, in particular of at least one element of the first set of graphical information. In this case, the second set of graphical information may be configured to supply information on the spatial and/or temporal resolution and/or size and/or positioning of the first set of graphical information, for example, by the graphical data storage medium. As a result, a display of the graphical presentation of the at least one virtual object in the presentation area of the second display unit may be enabled, advantageously adjusted to the first set of graphical information. As a result, an especially immersive and realistic display of the graphical presentation of the augmented reality, in particular of the at least one virtual object, may be enabled in the at least partial overlay with the presentation area of the second display unit.

In a further advantageous form of embodiment of the proposed presentation device, the first set of graphical information may contain a graphical presentation of first medical image data. Further, the first medical image data may contain a mapping and/or a model of a first area under examination of an object under examination.

The first medical image data may advantageously contain a spatially resolved mapping, in particular a time-resolved, two-dimensionally or three-dimensionally spatially resolved mapping, of the first area under examination, for example, of an anatomical region and/or an organ, in particular a hollow organ, and/or a bone structure, of the object under examination. Further, the first medical image data may contain a contrasted and/or segmented mapping of the first area under examination. The object under examination may be a human patient and/or an animal patient and/or an examination phantom.

Alternatively, or additionally, the first medical image data may contain a 2D and/or 3D model, in particular a central line model and/or a volume model, for example, a volume mesh model, of the first area under examination, in particular of the hollow organ.

The first medical image data may advantageously be recorded and/or supplied by a first medical imaging device. In this case, the first medical imaging device may be configured as a medical X-ray device and/or magnetic resonance system (MRT) and/or computed tomography system (CT) and/or positron emission tomography system (PET) and/or ultrasound device and/or endoscope, in particular a laparoscope and/or a bronchoscope, and/or a catheter.

The second display unit may advantageously be configured to display the first set of graphical information containing the graphical presentation of the first medical image data in the operating state of the presentation device. The processing unit may advantageously be configured to supply the graphical presentation of the augmented reality, such that the graphical presentation of the first medical image data displayed by the second display unit in the operating state of the presentation device is overlaid at least partially with the graphical presentation of the augmented reality, in particular the graphical presentation of the at least one virtual object.

The proposed form of embodiment may advantageously enable an at least partially overlaid display of the graphical presentation of the augmented reality with the graphical presentation of the first medical image data displayed in the presentation area of the second display unit in the operating state, wherein the augmented reality and/or the graphical presentation of the augmented reality is adjusted to the graphical presentation of the first medical image data.

In a further advantageous form of embodiment of the proposed presentation device, the second set of graphical information may contain at least one positional mark for the graphical presentation of the first medical image data. In this case, the processing unit may be configured to adjust the resolution and/or scaling and/or size and/or positioning of the graphical presentation of the at least one virtual object on the basis of the at least one positional mark.

The at least one positional mark may contain at least one graphical object, in particular an arrangement of multiple graphical objects, which corresponds to at least one geometric and/or anatomical feature in the graphical presentation of the first medical image data. In particular the second set of graphical information may contain multiple positional marks for the graphical presentation of the first medical image data. In this case, the multiple positional marks may each have at least one graphical object which corresponds in each case to at least one geometric and/or anatomical feature in the graphical presentation of the first medical image data. In this case, the multiple positional marks, in particular the multiple graphical objects, may be configured to be at least partially the same or different. The at least one geometric feature may include a line, in particular a contour and/or edge, and/or a corner and/or a contrast transition and/or a spatial arrangement of the aforementioned features. The at least one anatomical feature may include an anatomical landmark and/or a tissue border, for example, a wall of a vessel and/or organ, and/or an anatomical peculiarity, for example, a bifurcation and/or an ostium. The correspondence of the at least one graphical object to the at least one geometric and/or anatomical feature in the graphical presentation of the first medical image data may include a spatial correspondence in respect of the presentation area of the second display unit. In this case, the at least one graphical object may have a spatial positioning, in particular a spatial position and/or orientation, which corresponds to the spatial positioning of the corresponding at least one geometric and/or anatomical feature in the presentation area. The at least one graphical object can, thanks to its arrangement, advantageously represent the, in particular current, spatial positioning of the corresponding at least one geometric and/or anatomical feature of the graphical presentation of the first medical image data.

The at least one graphical object may be a virtual representation of the corresponding at least one geometric and/or anatomical feature of the graphical presentation of the first medical image data. For example, the at least one graphical object may be generated by a segmentation of the corresponding geometric and/or anatomical feature in the graphical presentation of the first medical image data. Alternatively, or additionally, the at least one graphical object may be a geometric object, in particular an abstract geometric object, for example, an arrow and/or a cross and/or a line, in particular a central line.

The second display unit may in the operating state of the presentation device advantageously display the at least one positional mark, in particular the at least one graphical object, in the presentation area so as to be hidden. The recording unit may advantageously be configured to capture the at least one positional mark, in particular the at least one graphical object, on the basis of the captured second set of graphical information. The capture of the at least one positional mark, in particular of the at least one graphical object, may include a capture of an, in particular current, spatial positioning, in particular position and/or orientation, of the positional mark, in particular of the at least one graphical object, in respect of the presentation area of the second display unit. In particular the recording unit may be configured for the capture, in particular the simultaneous capture, of multiple positional marks in the presentation area of the second display unit. As a result, the recording unit may advantageously be configured to capture, in particular indirectly, the spatial positioning, in particular the current spatial positioning, of the at least one geometric and/or anatomical feature of the graphical presentation of the first medical image data on the basis of the captured at least one positional mark.

The processing unit may advantageously further be configured to adjust the, in particular spatial and/or temporal, resolution and/or scaling and/or the size and/or positioning of the graphical presentation of the at least one virtual object on the basis of the at least one positional mark, in particular on the basis of the at least one graphical object. For example, the processing unit may be configured to adjust the spatial and/or temporal resolution and/or size and/or positioning of the graphical presentation of the at least one virtual object as a function of a spatial and/or temporal resolution and/or size and/or positioning of the at least one positional mark, in particular the at least one graphical object. In particular the processing unit may be configured to register the graphical presentation of the augmented reality, in particular of the at least one virtual object, with the graphical presentation of the first medical image data on the basis of the captured at least one positional mark.

Because in the operating state of the presentation device the at least one positional mark is displayed so as to be hidden for the user in the presentation area, the positional mark for the capture may be optimized by the recording unit, in particular without any influence on the first set of graphical information. As a result, a particularly reliable and at the same time precise adjustment of the graphical presentation of the at least one virtual object to the first set of graphical information may be enabled.

In a further advantageous form of embodiment of the proposed presentation device, the first medical image data may map a change, in particular a temporal and/or spatial change, in the first area under examination. In this case, the graphical presentation of the first medical image data may contain a scene. Further, the at least one positional mark may follow a movement of geometric and/or anatomical features in the scene.

In this case, the change, in particular the temporal and/or spatial change, may be a flow of contrast agent in a tissue and/or hollow organ, for example, a vessel, of the object under examination and/or a movement of at least one region, in particular of a tissue and/or organ, of the object under examination, for example, a respiratory movement and/or a cardiac movement, and/or a movement of a medical object, for example, of a surgical and/or diagnostic instrument.

The first medical image data may advantageously map the change in the first area under examination on a time-resolved basis. Further, the graphical presentation of the first medical image data may contain a scene. In this case, the scene may contain a temporal succession and/or sequence of multiple individual images, said individual images being recorded consecutively in time. In this case, the scene, in particular the multiple individual images, may map the change in the first area under examination.

The scene may contain the geometric and/or anatomical features of the graphical presentation of the first medical image data. In particular the multiple individual images may each contain the geometric and/or anatomical features of the graphical presentation of the first medical image data. In this case, the change in the first area under examination of the object under examination may be mapped by a change in at least one of the geometric and/or anatomical features in the scene. In this case, the change in the at least one of the geometric and/or anatomical features in the scene may be mapped as a movement of the at least one of the geometric and/or anatomical features in the presentation area of the second display unit.

The at least one positional mark, in particular the at least one graphical object, may advantageously follow the movement of the at least one geometric and/or anatomical feature in the scene. In this case, the at least one positional mark, which, in the operating state, the second display unit displays as hidden in the presentation area as part of the second set of graphical information, may follow the movement of the at least one geometric and/or anatomical feature in the presentation area of the second display unit. In particular the at least one graphical object may follow the movement of the respectively corresponding at least one geometric and/or anatomical feature. In other words, the spatial positioning, in particular the current spatial positioning, of the at least one positional mark may be adjusted, in particular uniformly, to the, in particular current, spatial positioning of the at least one geometric and/or anatomical feature in the scene, in particular continuously.

The recording unit may advantageously be configured to capture the movement of the at least one geometric and/or anatomical feature in the scene on the basis of the movement of the at least one positional mark. In this case, the recording unit may be configured for the, in particular repeated, capture of the second set of graphical information, in particular of the at least one positional mark. Moreover, the processing unit may advantageously be configured to adjust the resolution and/or scaling and/or size and/or positioning of the graphical presentation of the at least one virtual object on the basis of the captured movement of the at least one positional mark, in particular of the at least one graphical object. In particular the processing unit may be configured to register the graphical presentation of the at least one virtual object with the graphical presentation of the first medical image data on the basis of the captured at least one positional mark, in particular repeatedly. In this case, a latency between the display of the first and second sets of graphical information, in particular of the at least one positional mark, and the adjustment of the graphical presentation of the at least one virtual object may advantageously be minimized by the optical capture of the second set of graphical information, in particular of the at least one positional mark.

As a result, an adjustment, in particular a low-latency adjustment, of the graphical presentation of the augmented reality, in particular of the at least one virtual object, to the change in the first area under examination mapped in the scene may be enabled.

In a further advantageous form of embodiment of the proposed presentation device, the dataset may contain second medical image data. In this case, the second medical image data may contain a mapping and/or a model of a second area under examination of the object under examination. Further, the first and the second area under examination may coincide at least partially, in particular completely. Moreover, the processing unit may be configured to generate the augmented reality based on the second medical image data.

The second medical image data may advantageously contain a mapping, in particular a time-resolved, two-dimensionally or three-dimensionally spatially resolved mapping, of the second area under examination, for example, of an anatomical region and/or an organ, in particular a hollow organ, and/or a bone structure, of the object under examination. In this case, the first and the second area under examination may coincide at least partially, in particular completely. Further, the second medical image data may contain a contrasted and/or segmented mapping of the second area under examination. Further, the first and the second medical image data may map the object under examination at different or at least at partially the same recording times, for example, preoperatively or intraoperatively. Further, the first medical image data may contain a mapping, in particular an intraoperative mapping, of the medical imaging device for recording the second medical image data or vice versa.

Alternatively, or additionally, the second medical image data may contain a 2D and/or 3D model, in particular a central line model and/or a volume model, for example, a volume mesh model, of the second area under examination, in particular of the hollow organ.

The second medical image data may advantageously be recorded and/or supplied by a second medical imaging device. In this case, the second medical imaging device may be configured as a medical X-ray device and/or magnetic resonance system (MRT) and/or computed tomography system (CT) and/or positron emission tomography system (PET) and/or ultrasound device and/or endoscope, in particular a laparoscope and/or a bronchoscope, and/or a catheter. In particular the first and the second medical imaging device may be the same or different.

The processing unit may advantageously be configured to generate the augmented reality based on the second medical image data. For example, the processing unit may be configured to determine the at least one virtual object by segmentation and/or identification of anatomical objects, for example, a tissue region and/or an organ, in particular a hollow organ, and/or medical objects, for example, a surgical and/or diagnostic instrument and/or an implant, which are mapped in the second medical image data. The at least one virtual object may contain a mapping and/or virtual representation, for example, a 2D or 3D model, of the segmented and/or identified anatomical and/or medical object.

The processing unit may advantageously be configured to register the graphical presentation of the augmented reality, in particular the at least one virtual object, with the graphical presentation of the first medical image data on the basis of the captured second set of graphical information.

The proposed form of embodiment may advantageously enable an immersively overlaid display of the graphical presentation of the augmented reality with the graphical presentation of the first medical image data in the presentation area. In particular the display of the graphical presentation of the first medical image data may as a result remain uninfluenced by the display of the graphical presentation of the augmented reality.

A second aspect of the disclosure relates to a system having a proposed presentation device and a second display unit. In this case, the second display unit has a presentation area. Further, the second display unit is configured to display the first set of graphical information as visible and the second set of graphical information in the presentation area as a function of the first set of graphical information and as hidden.

The advantages of the proposed system substantially correspond to the advantages of the proposed presentation device for displaying a graphical presentation of an augmented reality. Features, advantages or alternative forms of embodiment mentioned here may likewise also be transferred to the other claimed subject matters and vice versa.

In a further advantageous form of embodiment of the proposed system, the system may further have a medical imaging device. In this case, the medical imaging device may be configured to record and/or supply the first medical image data. Further, the second display unit may be configured to display a graphical presentation of the first medical image data as visible in the presentation area as the first set of graphical information.

In a further advantageous form of embodiment of the proposed system, the medical imaging device may further be configured to record and/or supply the second medical image data.

In a further advantageous form of embodiment of the proposed system, the medical imaging device may be configured to be arranged at least partially in the object under examination.

The medical imaging device may be configured as an endoscope, in particular a laparoscope and/or a bronchoscope, and/or a catheter. In this case, a distal section of the medical imaging device may be arranged in an operating state of the system in the object under examination, in particular in a hollow organ of the object under examination.

A third aspect of the disclosure relates to a method for supplying a graphical presentation of an augmented reality. In this case, a relative positioning of a first display unit in respect of a presentation area of a second display unit is captured by a recording unit. Further, a first set of graphical information is displayed as visible in the presentation area of the second display unit and a second set of graphical information is displayed as a function of the first set of graphical information and as hidden. Furthermore, the second set of graphical information is captured by the recording unit. Moreover, a dataset is received. Further, the augmented reality is generated on the basis of the dataset. Further, the graphical presentation of the augmented reality is provided by a virtual mapping of the augmented reality to the presentation area of the second display unit on the basis of the relative positioning. Moreover, the augmented reality and/or the graphical presentation of the augmented reality is adjusted as a function of the second set of graphical information. Furthermore, the graphical presentation of the augmented reality is displayed in the presentation area of the second display unit by the first display unit in at least a partial overlay with the first set of graphical information. Further, the supply of the graphical presentation of the augmented reality includes a display of the graphical presentation of the augmented reality in the presentation area of the second display unit by the first display unit in at least a partial overlay with the first set of graphical information.

The advantages of the proposed method correspond substantially to the advantages of the proposed presentation device for displaying a graphical presentation of an augmented reality. Features, advantages or alternative forms of embodiment mentioned here may likewise also be transferred to the other claimed subject matters and vice versa. The device, in particular the presentation device and/or the system, may advantageously be configured to carry out a form of embodiment of the proposed method.

BRIEF DESCRIPTION OF THE DRAWINGS

Exemplary embodiments are represented in the drawings and are described in greater detail below. The same reference characters are used in different figures for the same features. In the drawings.

DETAILED DESCRIPTION

Figure 1:
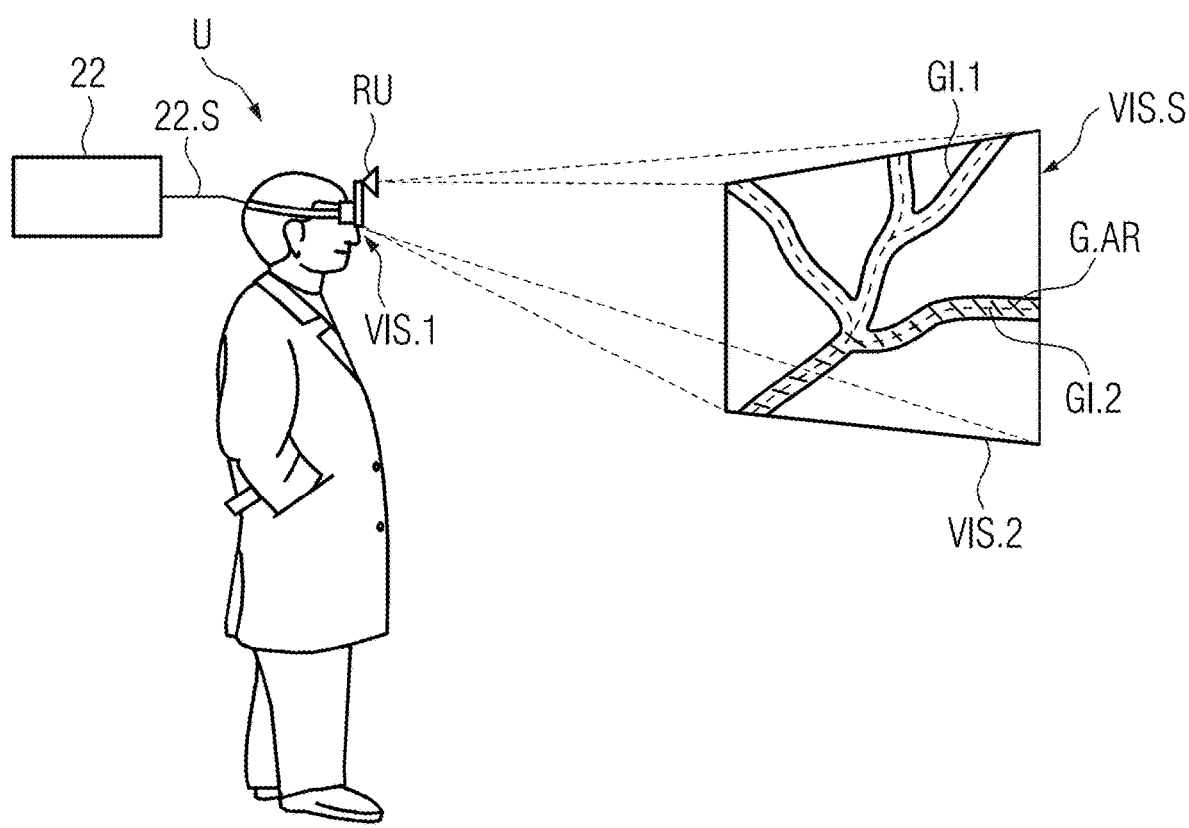
FIGS. 1 and 2 depict schematic representations of different advantageous forms of embodiment of a presentation device for displaying a graphical presentation of an augmented reality.

FIG. 1 schematically shows an advantageous form of embodiment of a proposed presentation device for displaying a graphical presentation of an augmented reality. In this case, the presentation device may have a recording unit RU, a first display unit VIS.1, and a processing unit 22. The first display unit VIS.1 may be configured at least partially to be transparent. In an operating state of the presentation device, a second display unit VIS.2 may in a presentation area VIS.S display a first set of graphical information GI.1 as visible and a second set of graphical information GI.2 as a function of the first set of graphical information GI.1 and as hidden. The second display unit VIS.2 may have a screen and/or monitor and/or projector and/or a projection area. In this case, the presentation area VIS.S of the second display unit VIS.2 may include the projection area and/or a display panel of the screen and/or of the monitor. In particular the presentation area VIS.S of the second display unit VIS.2 may include a bounded area, in which the first GI.1 and the second set of graphical information GI.2 may be displayed. In this case, the presentation area VIS.S of the second display unit VIS.2 may be flat, in particular level, or curved, at least in part, in particular completely.

Further, the recording unit RU may be configured to capture a relative positioning of the first display unit VIS.1 in respect of the presentation area VIS.S of the second display unit VIS.2. Moreover, the recording unit RU may be configured to capture the second set of graphical information GI.2. In this case, the recording unit RU may advantageously be integrated at least partially, in particular completely, into the first display unit VIS.1. In this case, the recording unit RU may have a defined, in particular stationary, arrangement in respect of the first display unit VIS.1. The recording unit RU may advantageously be integrated at least partially into the first display unit VIS.1, such that the second display unit VIS.2 in the operating state of the presentation device is arranged in a capture region of the recording unit RU. Further, the recording unit RU may have an optical sensor for the capture of the second set of graphical information GI.2. Moreover, the recording unit RU may have a further optical and/or electromagnetic and/or acoustic sensor for the capture of the relative positioning. In this case, the further optical sensor may be the same as or different from the optical sensor for the capture of the second set of graphical information GI.2.

The processing unit 22 may advantageously be configured to receive a dataset. In this case, the processing unit 22 may be coupled communicatively to the first display unit VIS.1 and the recording unit RU, for example, by a signal 22.S. Further, the processing unit 22 may be configured to generate the augmented reality AR based on the dataset. Moreover, the processing unit may be configured to supply a graphical presentation G.AR of the augmented reality AR by a virtual mapping of the augmented reality AR to the presentation area VIS.S of the second display unit VIS.2 on the basis of the relative positioning. Furthermore, the processing unit 22 may be configured to adjust the augmented reality AR and/or the graphical presentation of the augmented reality G.AR as a function of the second set of graphical information GI.2.

The first display unit VIS.1 may advantageously be configured to display the graphical presentation G.AR of the augmented reality AR in at least a partial overlay with the presentation area VIS.S of the second display unit VIS.2, in particular stereoscopically. For this, the first display unit VIS.1 may have a screen and/or a monitor and/or a projector and/or a projection area. The first display unit VIS.1 may advantageously be configured as glasses, in particular data glasses, and/or a helmet, in particular a data helmet, and/or a screen. Further, the first display unit VIS.1 may be configured to be portable, in particular to be carried by a user U within a field of view of the user U.

The first set of graphical information GI.1 may advantageously contain a graphical presentation of first medical image data. In this case, the first medical image data may have a mapping and/or a model of a first area under examination of an object under examination. For example, the first area under examination may contain a vessel section, for example, an artery and/or vein, of the object under examination. In this case, the first set of graphical information GI.1 may contain a graphical presentation of a mapping of the vessel section.

Further, the second set of graphical information GI.2 may contain at least one positional mark for the graphical presentation of the first medical image data. Moreover, the graphical presentation G.AR of the augmented reality AR may contain a graphical presentation of at least one virtual object of the augmented reality AR. The processing unit 22 may advantageously be configured to adjust a resolution and/or scaling and/or size and/or positioning of the graphical presentation of the at least one virtual object on the basis of the at least one positional mark.

The second set of graphical information GI.2 may have a positional mark embodied as a central line for the vessel section mapped in the first set of graphical information GI.1. Further, the augmented reality AR may contain a flow, in particular a simulated or measured flow, in particular a flow of contrast agent and/or a flow of blood, in the vessel section as the at least one virtual object. The processing unit 22 may advantageously be configured to adjust the augmented reality AR and/or the graphical presentation G.AR of the augmented reality AR on the basis of the at least one positional mark, in particular the central line. As a result, in the operating state of the presentation device a graphical presentation of the flow (illustrated in FIG. 1 as hatching) may advantageously be displayed with the graphical presentation of the vessel section in the presentation area VIS.S of the second display unit VIS.2 in at least a partial overlay.

The recording unit RU may advantageously be configured to capture the at least one positional mark on the basis of the captured second set of graphical information GI.2. The capture of the at least one positional mark may include a capture of a spatial positioning, in particular a current spatial positioning, in particular position and/or orientation, of the positional mark in respect of the presentation area VIS.S of the second display unit VIS.2.

Furthermore, the first medical image data may map a change over time in the first area under examination of the object under examination. In this case, the graphical presentation of the first medical image data may contain a scene. Further, the at least one positional mark may follow a movement of geometric and/or anatomical features of the graphical presentation of the first medical image data in the scene. The first medical image data may map a physiological movement in the first area under examination as the change over time. Alternatively, or additionally, the first medical image data may map a flow of contrast agent and/or a movement of a medical object, for example, of a surgical and/or diagnostic instrument, in the first area under examination.

The at least one positional mark may correspond to at least one geometric and/or anatomical feature in the graphical presentation of the first medical image data. The at least one geometric feature may include a line, in particular a contour and/or edge, and/or a corner and/or a contrast transition and/or a spatial arrangement of the aforementioned features. The at least one anatomical feature may include an anatomical landmark and/or a tissue border, for example, a wall of a vessel and/or organ, and/or an anatomical peculiarity, for example, a bifurcation and/or an ostium. The at least one positional mark in the exemplary embodiment as a central line may correspond to a vessel wall of the vessel section in the graphical presentation of the first medical image data, in particular spatially. In this case, the, in particular current, spatial positioning, in particular position and/or orientation, of the positional mark may be adjusted to the, in particular current, spatial positioning of the corresponding vessel wall in the graphical presentation of the first medical image data in the presentation area VIS.S of the second display unit VIS.2. As a result, the recording unit RU may advantageously be configured to capture the, in particular current, spatial positioning of the at least one geometric and/or anatomical feature of the graphical presentation of the first medical image data on the basis of the captured at least one positional mark, in particular indirectly.

Figure 2:
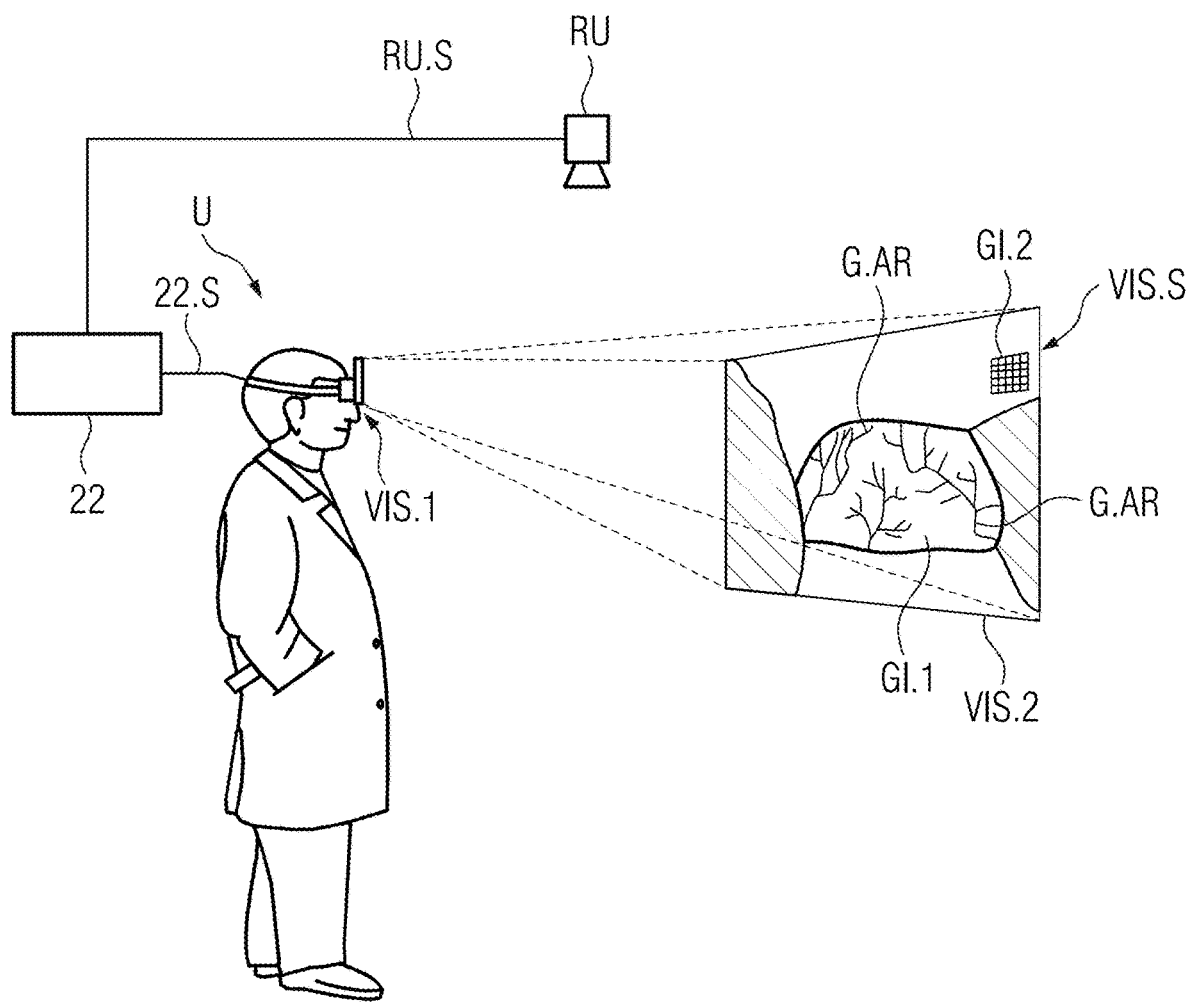

FIG. 2 shows a schematic representation of a further advantageous form of embodiment of a proposed presentation device. In this case, the recording unit RU may be arranged at a distance from the first VIS.1 and the second display unit VIS.2, in particular stationary in respect of a space in which in an operating state of the presentation device the first VIS.1 and the second display unit VIS.2 are arranged. Further, the recording unit RU may be configured to capture the relative positioning on the basis of representational features of the first VIS.1 and/or the second display unit VIS.2 and/or on the basis of the second set of graphical information GI.2. The recording unit RU may advantageously be arranged, in particular positioned, such that in the operating state of the presentation device the first VIS.1 and the second display unit VIS.2 are arranged in a capture region of the recording unit RU. Moreover, the recording unit RU may be configured to capture the relative positioning on the basis of representational features of the first and the second display unit VIS.2 and/or on the basis of the second set of graphical information GI.2.

In the form of embodiment represented schematically in FIG. 2, the first medical image data may map a lumen of a hollow organ of the object under examination. In this case, the first medical image data may be supplied, in particular in real time, by a medical imaging device which is embodied as an endoscope or catheter and which in the operating state of the presentation device is arranged in the object under examination, in particular in the hollow organ of the object under examination.

The second set of graphical information GI.2 may advantageously contain a graphical data storage medium. In this case, the graphical data storage medium may contain information on the first set of graphical information. In this case, the graphical data storage medium may be configured as a barcode and/or quick response code (QR code). The graphical data storage medium may advantageously, in particular by the graphical encoding, supply the information on the first set of graphical information GI.1 to the recording unit RU. In this case, the recording unit RU may advantageously be configured to decode the captured graphical data storage medium.

The information on the first set of graphical information GI.1 may contain origin information and/or presentation information on the first set of graphical information GI.1. For example, the origin information may contain positioning information which describes a spatial position and/or orientation and/or pose and/or a spatial recording region of the medical imaging device, in particular of the endoscope and/or catheter, for recording and/or for supplying the first medical image data.

The dataset may advantageously contain second medical image data, wherein the second medical image data contains a mapping and/or a model of a second area under examination of the object under examination. In this case, the first and the second area under examination may at least partially coincide. For example, the second medical image data may contain a vessel section of a tissue, for example, of a tumor tissue, which adjoins the lumen of the hollow organ mapped in the first medical image data. Further, the processing unit 22 may be configured to generate the augmented reality AR based on the second medical image data. Moreover, the processing unit 22 may be configured to determine the at least one virtual object on the basis of the second set of graphical information GI.2, in particular on the basis of the information on the first set of graphical information GI.1 supplied by the graphical data storage medium. In this case, a mapping and/or a model of the vessel section may be determined as the at least one virtual object.

Figure 3:
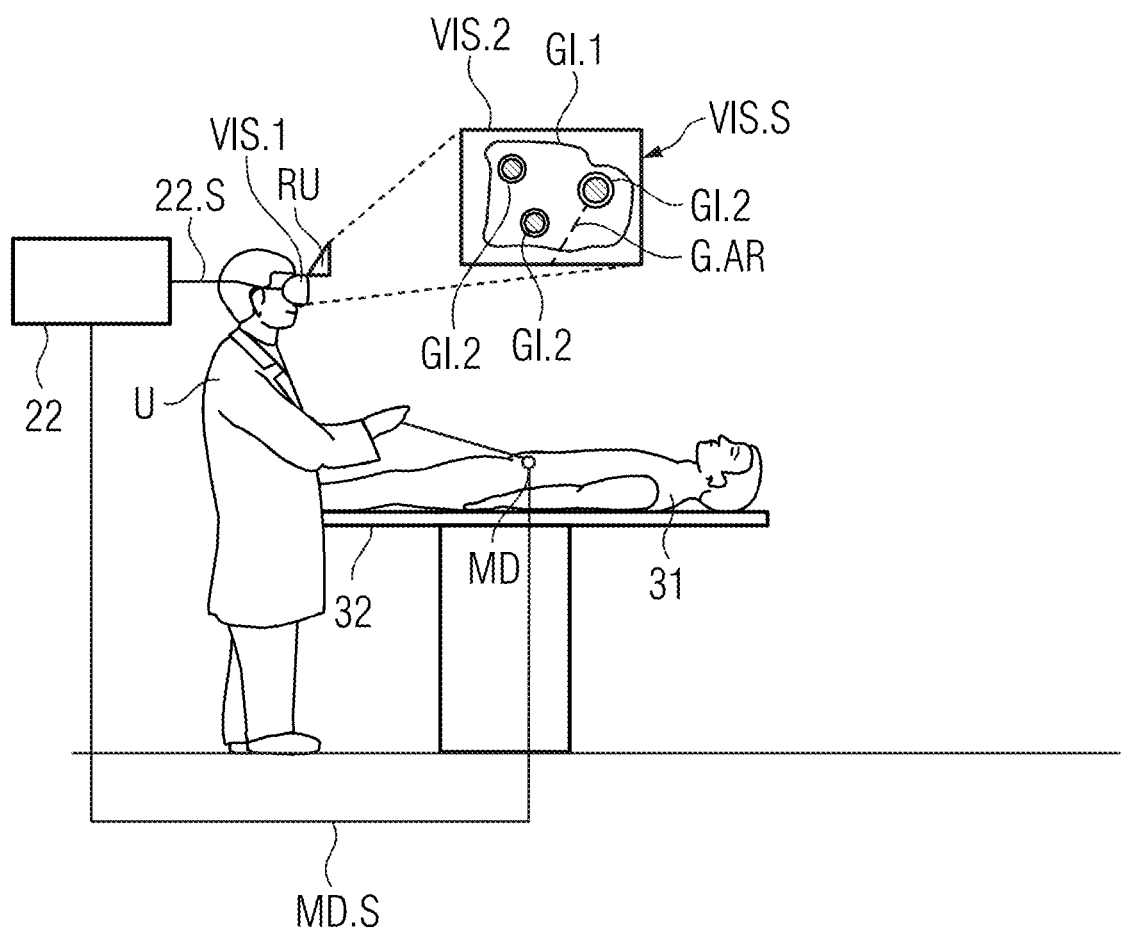
FIG. 3 depicts a schematic representation of an advantageous form of embodiment of a proposed system.

FIG. 3 schematically represents an advantageous form of embodiment of a proposed system. In this case, the system may have a proposed presentation device and the second display unit VIS.2. In this case, the second display unit VIS.2 may have the presentation area VIS.S. Moreover, the second display unit VIS.2 may be configured to display the first set of graphical information GI.1 as visible and the second set of graphical information GI.2 as a function of the first set of graphical information GI.1 as hidden in the presentation area VIS.S. The system may advantageously further have a medical imaging device MD. In this case, the medical imaging device MD may be configured to be arranged at least partially in an object under examination 31. In this case, the object under examination 31 may be arranged on a patient examination device 32. In particular the medical imaging device MD may in an operating state of the system be arranged at least partially within the first and/or the second area under examination. Moreover, the medical imaging device MD may be configured to record and/or supply the first and/or the second medical image data.

In the form of embodiment of the proposed system represented schematically in FIG. 3, the first set of graphical information GI.1 may contain a graphical presentation of the first medical image data. The first medical image data may map a lumen of a hollow organ of the object under examination 31. In this case, the lumen may have multiple ostia (illustrated by hatching). Further, the second set of graphical information GI.2 in each case contains a positional mark for the ostia. The processing unit 22 may advantageously be configured to determine path planning for the medical imaging device MD as the at least one virtual object on the basis of the second set of graphical information GI.2. In this case, the graphical presentation G.AR of the augmented reality AR may contain a graphical presentation of the path planning, for example, as a workflow instruction to the user U.

Figure 4:
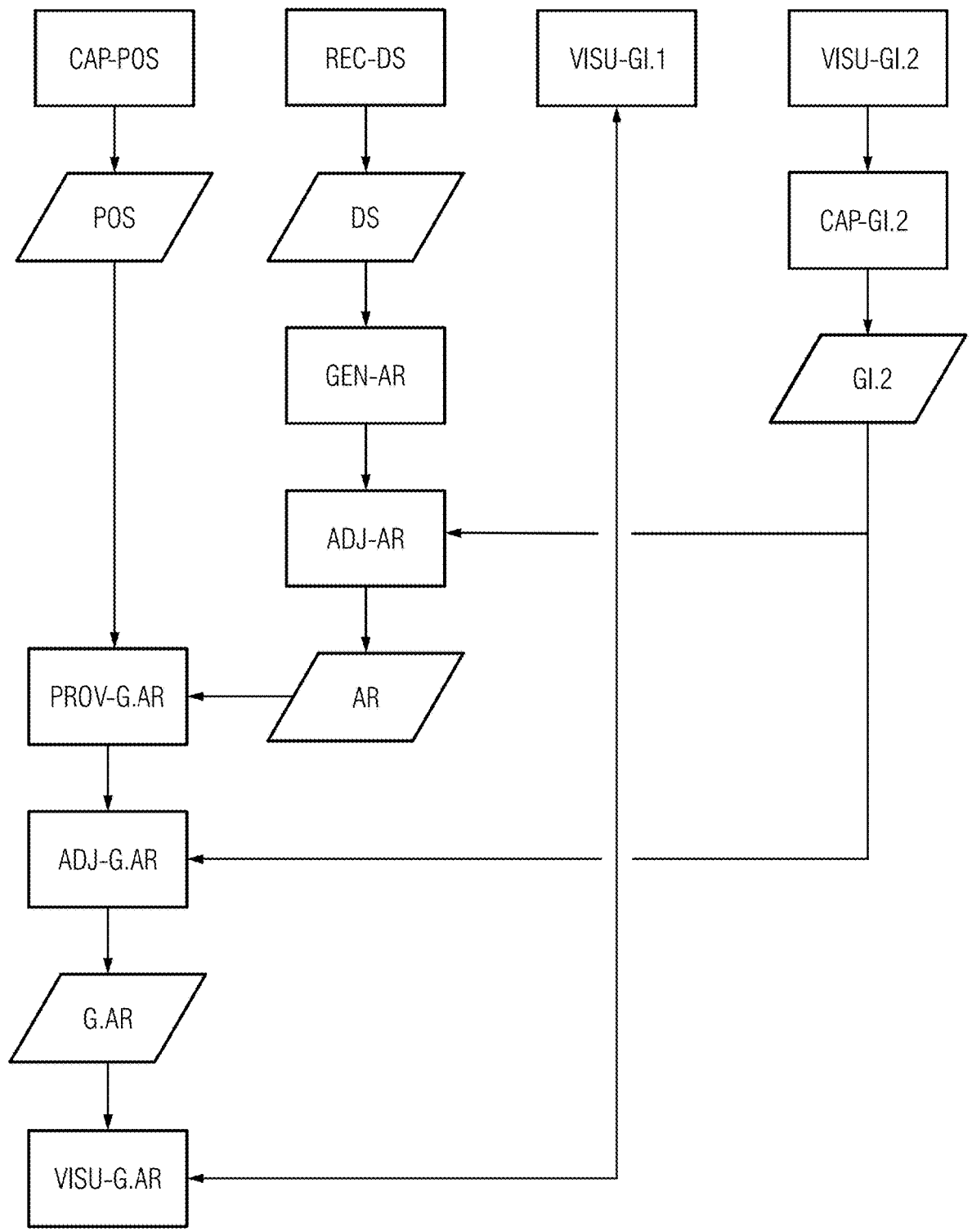
FIG. 4 depicts a schematic representation of a proposed method for the supply of a graphical presentation of an augmented reality.

FIG. 4 shows a schematic representation of an advantageous form of embodiment of a proposed method for the supply PROV-G.AR of a graphical presentation G.AR of an augmented reality AR. In this case, the relative positioning POS of the first display unit VIS.1 in respect of the presentation area VIS.S of the second display unit VIS.2 may be captured by the recording unit RU. In this case, the first set of graphical information GI.1 may be displayed VISU-GI.1 as visible in the presentation area VIS.S of the second display unit VIS.2. Moreover, the second set of graphical information GI.2 may be displayed as a function of the first set of graphical information GI.1 and as hidden in the presentation area VIS.S of the second display unit VIS.2. Furthermore, the second set of graphical information GI.2 may be captured CAP-GI.2 by the recording unit RU. Further, the dataset DS may be received REC-DS. Moreover, the augmented reality AR based on the dataset may be generated GEN-AR. Furthermore, the graphical presentation G.AR of the augmented reality AR may be supplied PROV-G.AR by the virtual mapping of the augmented reality AR to the presentation area VIS.S of the second display unit VIS.2 on the basis of the relative positioning POS. Further, the augmented reality AR and/or the graphical presentation G.AR of the augmented reality AR may be adjusted ADJ-AR, ADJ-G.AR as a function of the second set of graphical information GI.2. Following this, the graphical presentation G.AR of the augmented reality AR may be displayed VISU-G.AR by the first display unit VIS.1 in at least a partial overlay with the first set of graphical information GI.1 in the presentation area VIS.S of the second display unit VIS.2.

The schematic representations contained in the figures described are not at all to scale or in proportion.

In conclusion, it is once again pointed out that the methods and devices described in detail above are merely exemplary embodiments that may be modified in a wide variety of ways by the person skilled in the art, without departing from the scope of the disclosure. Further, the use of the indefinite article "a" or "an" does not rule out that the features in question may also be present multiple times. Likewise, the terms "unit" and "element" do not rule out that the components in question include multiple interacting subcomponents, which where appropriate may also be spatially distributed.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A presentation device for display of a graphical presentation of an augmented reality, the presentation device comprising:
   a recording unit;
   a first display unit; and
   a processing unit,
   wherein, in an operating state of the presentation device, a second display unit in a presentation area is configured to display a first set of graphical information as visible and display a second set of graphical information as a function of the first set of graphical information and as hidden,
   wherein the recording unit is configured to:
      capture a relative positioning of the first display unit in respect of the presentation area of the second display unit, and
      capture the second set of graphical information,
   wherein the processing unit is configured to:
      receive a dataset,
      generate the augmented reality based on the dataset,
      supply the graphical presentation of the augmented reality by a virtual mapping of the augmented reality to the presentation area of the second display unit based on the relative positioning, and
      adjust the augmented reality and/or the graphical presentation of the augmented reality as a function of the second set of graphical information,
   wherein the first display unit is configured to be at least partially transparent, and
   wherein the first display unit is configured to display the graphical presentation of the augmented reality in at least a partial overlay with the presentation area of the second display unit.

2. The presentation device of claim 1, wherein the recording unit is arranged at a distance from the first display unit and the second display unit, or
   wherein the recording unit is at least partially integrated into the first display unit.

3. The presentation device of claim 1, wherein the recording unit comprises an optical sensor for the capture of the second set of graphical information.

4. The presentation device of claim 1, wherein the recording unit comprises an optical sensor, an electromagnetic sensor, an acoustic sensor, or a combination thereof for the capture of the relative positioning.

5. The presentation device of claim 1, wherein the recording unit is configured to capture the relative positioning based on representational features of the first display unit, features of the second display unit, the second set of graphical information, or a combination thereof.

6. The presentation device of claim 1, wherein the second set of graphical information comprises a graphical data storage medium, and
   wherein the graphical data storage medium comprises information on the first set of graphical information.

7. The presentation device of claim 1, wherein the graphical presentation of the augmented reality comprises a graphical presentation of at least one virtual object of the augmented reality, and wherein the processing unit is configured to:
   determine the at least one virtual object based on the second set of graphical information,
   adjust a resolution, a scaling, a size, a positioning, or a combination thereof of the graphical presentation of the at least one virtual object based on the second set of graphical information, or
   a combination thereof.

8. The presentation device of claim 1, wherein the first set of graphical information comprises a graphical presentation of first medical image data, and
   wherein the first medical image data comprises a mapping, a model, or a combination thereof of a first area under examination of an object under examination.

9. The presentation device of claim 8, wherein the second set of graphical information contains at least one positional mark for the graphical presentation of the first medical image data, and
   wherein the processing unit is configured to adjust a resolution, a scaling, a size, a positioning, or a combination thereof of a graphical presentation of at least one virtual object of the augmented reality based on the at least one positional mark.

10. The presentation device of claim 9, wherein the first medical image data maps a change in the first area under examination,
    wherein the graphical presentation of the first medical image data comprises a scene, and
    wherein the at least one positional mark follows a movement of geometric and/or anatomical features of the graphical presentation of the first medical image data in the scene.

11. The presentation device of claim 8, wherein the dataset contains second medical image data,
    wherein the second medical image data comprises a mapping, a model, or a combination thereof of a second area under examination of the object under examination,
    wherein the first area under examination and the second area under examination coincide at least partially, and
    wherein the processing unit is configured to generate the augmented reality based on the second medical image data.

12. A system comprising:
    a presentation device having a recording unit, a first display unit, and a processing unit; and
    a second display unit,
    wherein the recording unit is configured to:
       capture a relative positioning of the first display unit in respect of a presentation area of the second display unit, and
       capture a second set of graphical information,
    wherein the processing unit is configured to:
       receive a dataset,
       generate an augmented reality based on the dataset,
       supply a graphical presentation of the augmented reality by a virtual mapping of the augmented reality to the presentation area of the second display unit based on the relative positioning, and
       adjust the augmented reality and/or the graphical presentation of the augmented reality as a function of the second set of graphical information,
    wherein the first display unit is configured to be at least partially transparent,
    wherein the first display unit is configured to display the graphical presentation of the augmented reality in at least a partial overlay with the presentation area of the second display unit,
    wherein the second display unit has a presentation area,
    wherein the second display unit is configured, in the presentation area, to display a first set of graphical information as visible and display the second set of graphical information as a function of the first set of graphical information and as hidden.

13. The system of claim 12, further comprising:
    a medical imaging device,
    wherein the first set of graphical information comprises a graphical presentation of first medical image data,
    wherein the first medical image data comprises a mapping, a model, or a combination thereof of a first area under examination of an object under examination,
    wherein the medical imaging device is configured to record and/or supply the first medical image data,
    wherein the second display unit is configured to display a graphical presentation of the first medical image data as the first set of graphical information as visible in the presentation area.

14. The system of claim 13, wherein the processing unit is configured to generate the augmented reality based on second medical image data,
    wherein the medical imaging device is further configured to record and/or supply the second medical image data,
    wherein the second medical image data comprises a mapping, a model, or a combination thereof of a second area under examination of the object under examination, and
    wherein the first area under examination and the second area under examination coincide at least partially.

15. The system of claim 14, wherein the medical imaging device is configured to be arranged at least partially in the object under examination.

16. The system of claim 13, wherein the medical imaging device is configured to be arranged at least partially in the object under examination.

17. A method for supply of a graphical presentation of an augmented reality, the method comprising:
    capturing, by a recording unit, a relative positioning of a first display unit in respect of a presentation area of a second display unit;
    displaying, in the presentation area, a first set of graphical information as visible and a second set of graphical information as a function of the first set of graphical information and as hidden, wherein the second set of graphical information is captured by the recording unit;
    receiving a dataset;
    generating the augmented reality based on the dataset;
    supplying the graphical presentation of the augmented reality by a virtual mapping of the augmented reality in the presentation area of the second display unit based on the relative positioning; and
    adjusting the augmented reality and/or the graphical presentation of the augmented reality as a function of the second set of graphical information,
    wherein the supplying of the graphical presentation of the augmented reality comprises a display of the graphical presentation of the augmented reality by the first display unit in at least a partial overlay with the first set of graphical information in the presentation area of the second display unit.

* * * * *